United States Patent [19]
Murphy

[11] Patent Number: 5,226,884
[45] Date of Patent: Jul. 13, 1993

[54] SINGLE USE SYRINGE

[76] Inventor: Gary Murphy, 4621 Hamlin, Corpus Christi, Tex. 78411

[21] Appl. No.: 945,912

[22] Filed: Sep. 17, 1992

[51] Int. Cl.$^5$ .............................................. A61M 5/00
[52] U.S. Cl. ..................................... 604/110; 604/218
[58] Field of Search ............ 604/110, 187, 218, 220, 604/228, 192, 198

[56] References Cited

U.S. PATENT DOCUMENTS

| | | | |
|---|---|---|---|
| 4,668,223 | 5/1987 | Grotenhuis | 604/218 X |
| 4,731,068 | 3/1988 | Hesse | 604/218 X |
| 4,781,684 | 11/1988 | Trenner | 604/110 |
| 4,820,272 | 4/1989 | Palmer | 604/110 |
| 4,878,899 | 11/1989 | Plouff | 604/110 |
| 4,946,441 | 8/1990 | Laderoute | 604/110 |
| 5,066,279 | 11/1991 | Russell | 604/110 |
| 5,084,018 | 1/1992 | Tsao | 604/110 |
| 5,114,405 | 5/1992 | Winter | 604/110 |

FOREIGN PATENT DOCUMENTS

| | | | |
|---|---|---|---|
| 2646086 | 10/1990 | France | 604/228 |
| 2653340 | 4/1991 | France | 604/110 |

Primary Examiner—John D. Yasko
Attorney, Agent, or Firm—Richard C. Litman

[57] ABSTRACT

A single use syringe which includes a cylindrical barrel having integral finger grips and a first bore, a cylindrical insert having a chamfered bottom end and a second bore, the cylindrical insert being located in the first bore with a space between the chamfered bottom end and the base of the cylindrical barrel sufficient to receive a resilient plunger, a needle or cannula connected to the bottom of the cylindrical barrel, and a cylindrical back stop disposed in the first bore at the top of the barrel. The plunger is releasably connected to a plunger rod by a ball and socket arrangement. The plunger in passing from the first bore to the second bore expands to fill the second bore. The expanded plunger is stopped from retraction and disengaged from the plunger rod by engagement of the plunger with the chamfered bottom end of the cylindrical insert during retraction of the plunger rod. Retraction of the plunger rod is limited by engagement of a transverse cylindrical plate integral with the plunger rod adjacent the plunger with a bottom surface of the cylindrical back stop. A cap is provided to cover the needle, the cap having a funnel-shaped open end, an elongated tube, and a transverse plate integral with the tube to engage the tip of the needle.

4 Claims, 3 Drawing Sheets

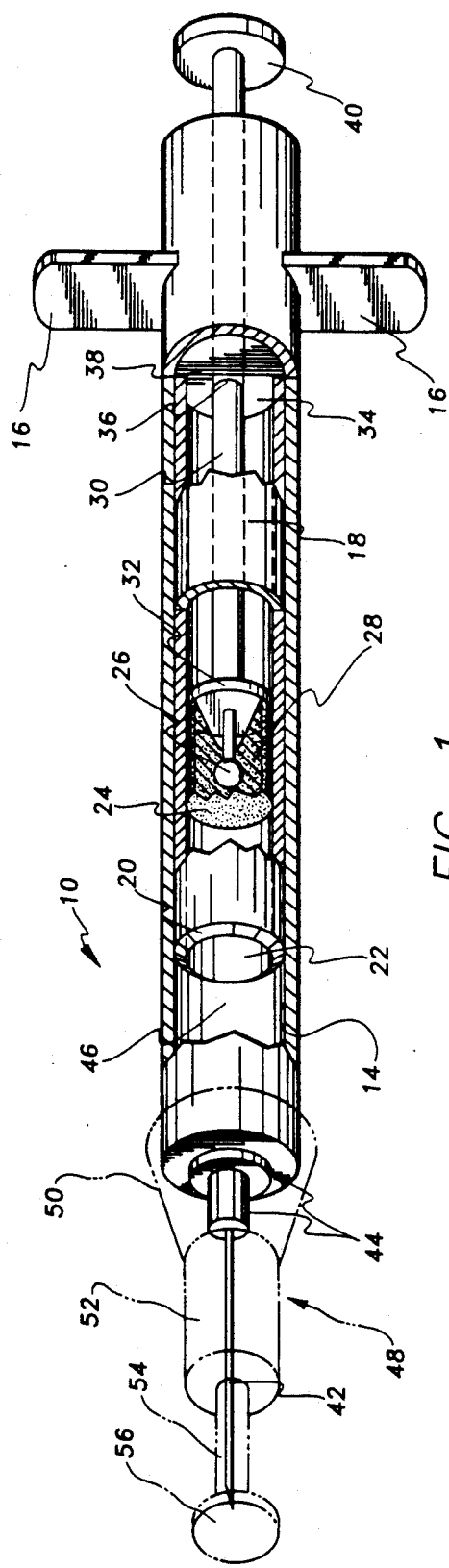
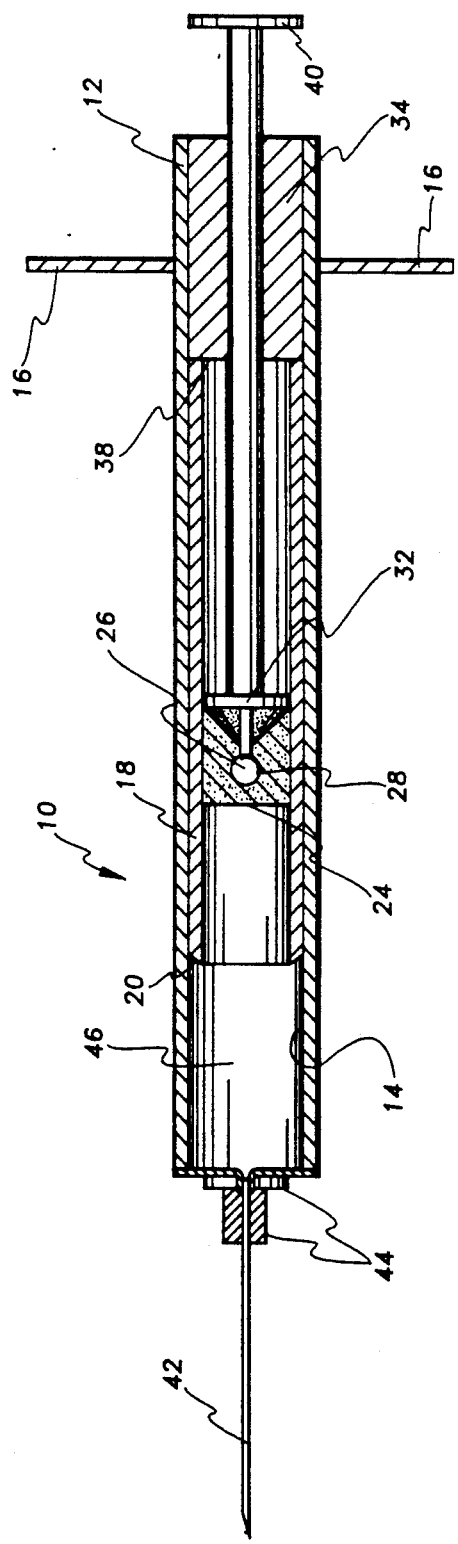
FIG. 1
FIG. 2

SINGLE USE SYRINGE

BACKGROUND OF THE INVENTION

1. Field of the Invention

The present invention relates to a single use syringe. More specifically, this invention relates to an arrangement designed to separate the plunger from the plunger rod after a single use to thereby prevent needle sharing among drug addicts or patients, which has been a major contributor to the transmittal of viral infections such as AIDS.

This invention also includes a cap to be placed over a needle subsequent to syringe use to prevent a noninfected person from being pricked with the needle after its use. Such accidents usually occur when a nurse, doctor, lab technician, relative or friend draws a blood sample or administers an injection to a known or unknown HIV infected person.

The syringe of the present invention also includes a tube-type backstop which prevents removal of the plunger rod from the barrel of the syringe, thereby precluding the interchange of parts between syringes.

2. Description of the Prior Art

Single use syringes are known in the prior art. U.S. Pat. No. 4,820,272 issued Apr. 11, 1989 to Michele M. Palmer discloses a non-reusable hypodermic syringe which uses downwardly slanted teeth disposed internally of the syringe barrel to limit movement of the plunger and the piston connected thereto to a single direction, the teeth preventing retraction of the plunger in the opposite direction.

U.S. Pat. No. 4,878,899 issued Nov. 7, 1989 to Frederick L. Plouff discloses a disposable syringe for one time use comprising a plurality of resilient pins disposed longitudinally of a syringe barrel and internally thereof, and biased to engage the plunger or piston once the plunger or piston has passed the ends of the resilient pins, the pins serving to prevent the retraction of the plunger.

U.S. Pat. No. 5,084,018 issued Jan. 28, 1992 to Chien-Hua Tsao discloses a safety syringe wherein the end of the plunger and the needle collapse into the hollow plunger rod after the plunger rod has been displaced to the end of the barrel.

U.S. Pat. No. 5,114,405 issued May 19, 1992 to Douglas A. Winter discloses a single use, tamper resistant syringe having a plunger slidable within a cylinder retained within a barrel, the cylinder including a pair of biased dogs which are engageable with a surface of the plunger when fully depressed to prevent retraction of the plunger, the dogs engaging a top surface of a cap or piston mounted on the plunger to separate the plunger and the cap or piston when not fully depressed to prevent removal of the plunger and the cap or piston when not fully depressed.

French Patent No. 2,646,086 issued Oct. 26, 1990 to Francis Pons discloses a plastic syringe which is separable from a plunger after a single use by disengaging convergent fingers integral with a piston by a camming means on the plunger.

French Patent No. 2,653,340 issued Apr. 26, 1991 to Monie Jean discloses a single use syringe having a separable ring and conical coupling whereby a piston is separated from a plunger after the plunger has been fully depressed.

U.S. Pat. No. 5,066,279 issued Nov. 19, 1991 discloses a protective sheath for encasing a hypodermic needle before and after use.

None of the foregoing patents, taken either alone or in combination, disclose or suggest the instant invention as described and claimed below.

SUMMARY AND OBJECTS OF THE INVENTION

The syringe of this invention comprises a barrel, a resilient plunger releasably mounted on a plunger rod disposed within a barrel, a cylindrical insert having a tapered bottom end and a bore sufficient to enable the resilient plunger to travel within the bore without being dislodged from the plunger rod, the tapered bottom end being spaced from the bottom end of the barrel a distance greater than the height of the plunger, and a cylindrical back stop disposed in the top of the barrel and having a bore slightly larger than the plunger rod to axially move relative to the barrel and back stop, the plunger rod having a transverse cylindrical plate integral therewith adjacent to the plunger and having a diameter slightly smaller than the bore within the cylindrical insert, whereby the plunger rod can be pulled out of the barrel only until the transverse plate engages the bottom surface of the cylindrical back stop which prevents total removal of the plunger rod and plunger from the barrel. A needle is suitably attached to the base of the barrel, a finger grip is integral with the barrel near the top thereof, and the plunger rod has a handle portion which may be grasped to move the plunger rod and plunger within the barrel.

In use, the plunger rod and plunger may initially be pulled out from the barrel until the transverse cylindrical plate engages the bottom surface of the cylindrical back stop so as to draw in fluid through the needle. The needle is then inserted into the patient and the fluid is injected by depressing the handle on the plunger rod while pulling on the finger grip. Once the plunger passes the tapered bottom end of the cylindrical insert, the top of the resilient plunger expands uniformly to engage the inner wall of the barrel. Because of this expansion, any attempt to retract the plunger will be prevented because of interference with the tapered bottom end of the cylindrical insert, thus rendering the syringe useless for further injections. Because of this interference, further pulling on the plunger rod will result in the separation of the plunger from the rod.

The syringe, after it has been used once, is ready for disposal. A needle cover is provided to shield the needle so that the user is protected from inadvertently being stuck. The cover includes a cylindrical sheath having a base into which the needle may be stuck without penetration of the base, and a funnel-shaped opposite end which helps to guide the needle into the base while protecting the user's hand when grasped.

It is an object of the invention to provide a syringe intended to be used only once and then discarded.

It is a further object of the invention to provide a syringe having a plunger and plunger rod which are separable after a single use to thereby prevent multiple uses.

It is a still further object of the invention to provide a syringe with a means to limit the degree of retraction of the plunger rod during initial use.

It is an additional object of the invention to provide a syringe needle with a cover to protect a handler's fingers before and after use so as to prevent inadvertent pricking of the handler's fingers.

It is an object of the invention to provide improved elements and arrangements thereof in an apparatus for the purposes described which is inexpensive, dependable and fully effective in accomplishing its intended purposes.

These and other objects of the present invention will become readily apparent upon further review of the following specification and drawings.

BRIEF DESCRIPTION OF THE DRAWINGS

FIG. 1 is a perspective view partially in section showing the several elements of the invention in assembled form.

FIG. 2 is a sectional view showing the several elements of the invention in assembled form.

Similar reference characters denote corresponding features consistently throughout the attached drawings.

DETAILED DESCRIPTION OF THE PREFERRED EMBODIMENT

Figure 3:
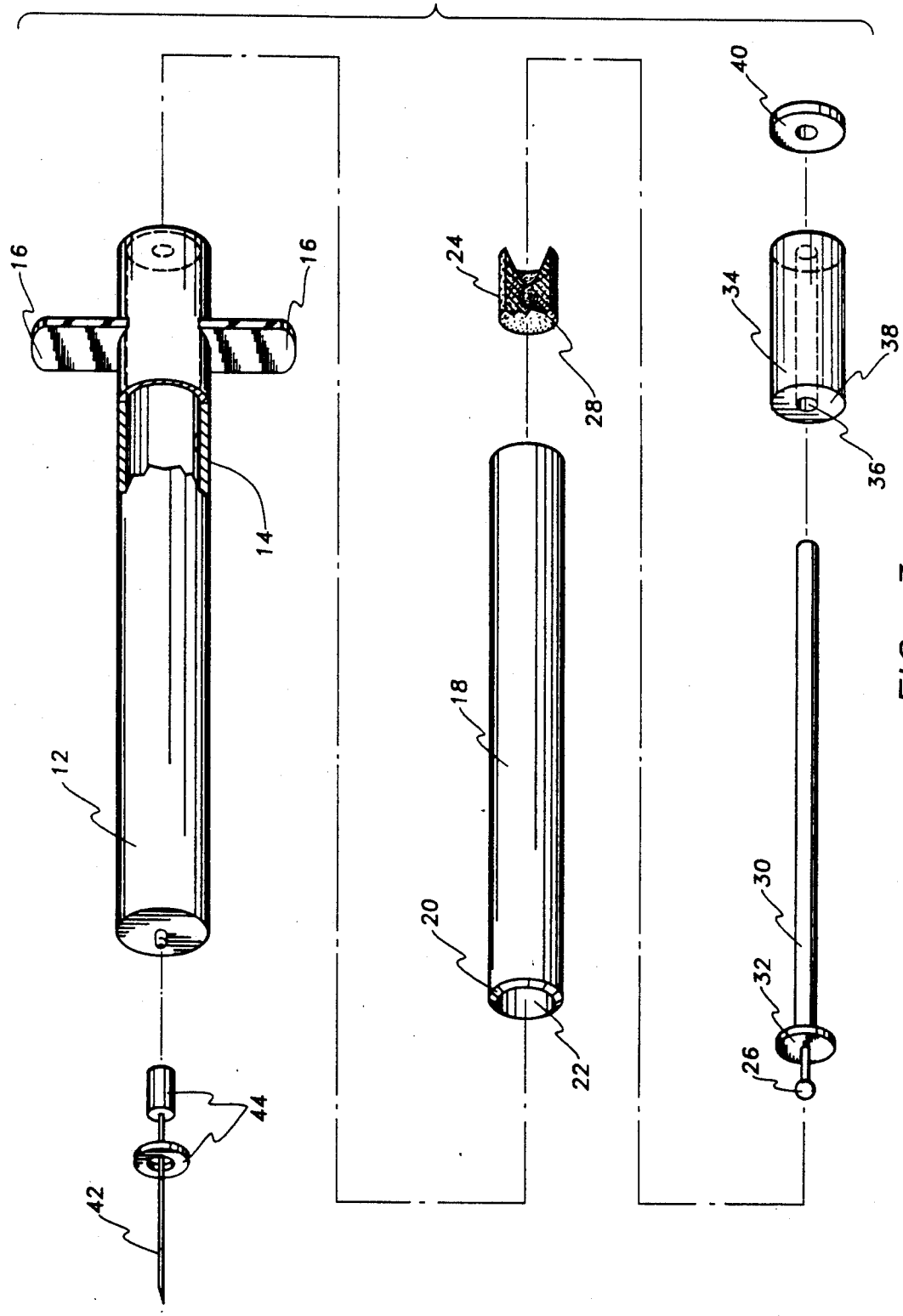
FIG. 3 is an exploded perspective view of the invention.

Before explaining in detail the present invention, it is to be understood that the invention is not limited to its application to the details of construction and arrangement of parts illustrated in the accompanying drawings, since the invention is capable of other embodiments and of being protected or carried out in various ways. Also, it is to be understood that the phraseology and terminology employed herein is for the purpose of description and net limitation.

The assembled syringe 10 shown best in FIGS. 1 and 2 includes am elongated barrel 12 having an inner bore 14 and finger grips 16 integral with barrel 12 at one end thereof. A cylindrical insert 18 having a chamfer taper 20 at one end is suitably located within bore 14 of barrel 12 as by friction fit or by adhesive means, not shown, the insert 18 in turn having a second bore 22 with a diameter sufficient to enable a plunger 24 to move therethrough. Plunger 24 is releasably connected through a ball 26 and socket 28 to a plunger rod 30. A transverse cylindrical plate 32 is integral with plunger rod 30, adjacent to plunger 24, the purpose of which is explained below.

A cylindrical back stop 34 is disposed within inner bore 14 at the top end of barrel 12. Back stop 34 has a bore 36 with a diameter slightly larger than the diameter of plunger rod 30 to enable axial movement of plunger rod 30 while preventing removal of plunger rod 30 from barrel 12 through engagement of transverse cylindrical plate 32 with the bottom surface 38 of cylindrical back stop 34. Plunger rod 30 has a handle 40 thereon to ease manipulation of plunger rod 30.

A cannula or needle 42 is suitably connected to the bottom end of barrel 12 by any conventional connection means 44. A space 46 is provided between the chamfered end 20 of cylindrical insert 18 and the bottom end of barrel 12, space 46 having a height greater than the height of plunger 24. A cap 48 is provided for covering the needle 42 both before and after the syringe 10 is used. The cap 48 comprises a funnel-like open end 50 which helps to guide the needle 42 into an elongated tube 52 having a bore 54 therethrough closed by a transverse cylindrical plate 56 which may be jabbed by the tip of needle 42.

Figure 5A:
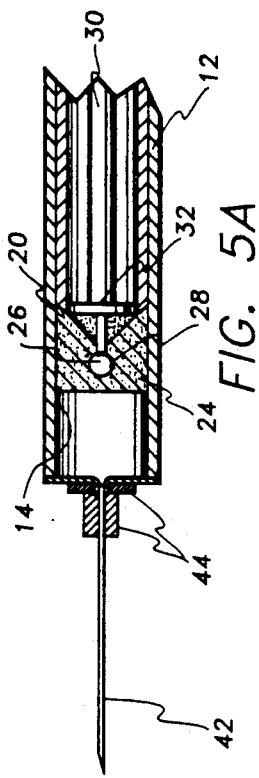
FIGS. 5A, 5B and 5C sequentially illustrate the sequential coaction between the plunger and the cylindrical insert to disengage the plunger from the plunger rod after a single use.
Figure 5B:
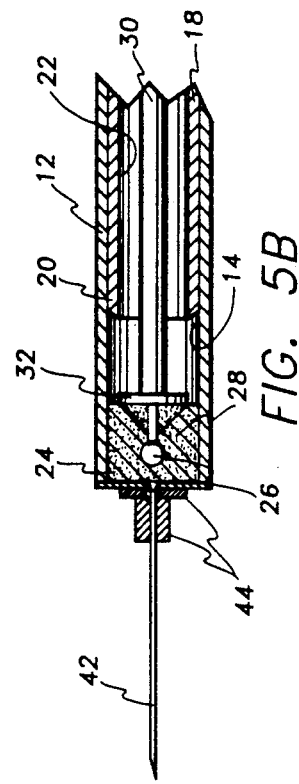
Figure 4:
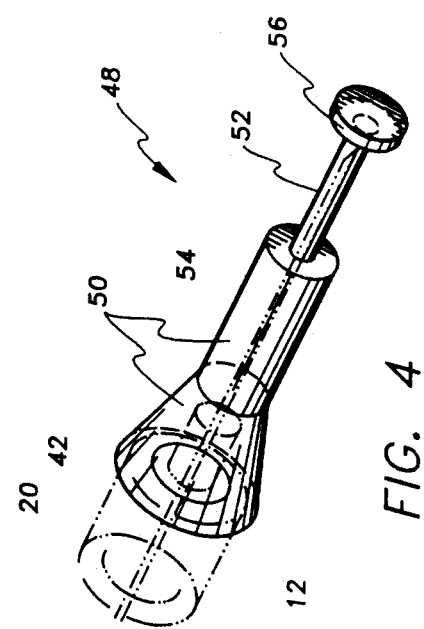
FIG. 4 is a perspective view of a cap for covering a needle before and after use.
Figure 5C:
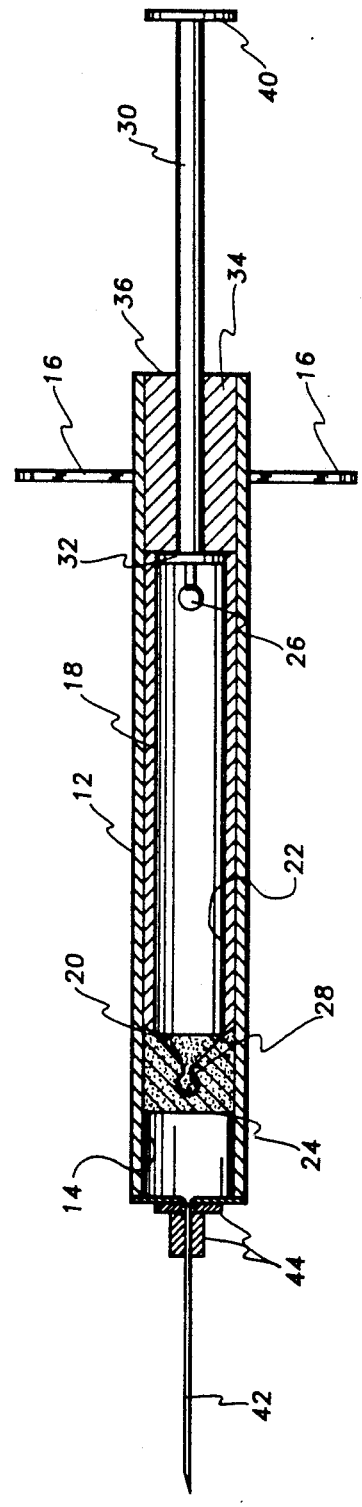

When the syringe 10 is to be used, cap 48 is first removed. So long as plunger 24 remains in second bore 22, it can be retracted to draw fluid into barrel 12 through needle 42. Thereafter, by grasping handle 40 and finger grips 16, plunger 24 and plunger rod 30 can be moved toward the bottom of barrel 12. When plunger 24 moves past chamfer or taper 20 of insert 18, a resilient top portion of plunger 24 expands to fill inner bore 14. Any subsequent attempt to pull plunger rod 30 out of barrel 12 will result in dislodging or separating plunger 24 from plunger rod 30. This sequence is shown in FIGS. 5A, 5B and 5C. In FIG. 5A, plunger 24 has moved below the taper or chamfer 20 at the base of cylindrical insert 18, and has expanded to fill inner bore 14. In FIG. 5B, the movement of plunger 24 continues until stopped by the bottom of barrel 12. In FIG. 5C, plunger rod 30 has been retracted until plate 32 has engaged bottom surface 38 of back stop 34. Plunger 24 is prevented from following plunger rod 30 by engagement of the top thereof with chamfer or tapes 20 and, accordingly, plunger 24 has been disengaged from rod 30 and remains confined in space 46. Because plunger 24 has been dislodged from plunger rod 30, syringe 10 is now disabled and eligible for discarding. Cap 48 is provided to cover needle 42 prior to discarding syringe 10 so as to prevent handlers from being accidentally pricked by the needle.

It is to be understood that the present invention is not limited to the sole embodiment described above, but encompasses any and all embodiments within the scope of the following claims.

I claim:

1. A single use syringe comprising:
    a cylindrical barrel having an inner bore;
    a cylindrical insert having a chamfered bottom end secured within said inner bore;
    a second bore within said cylindrical insert;
    a resilient plunger disposed within said second bore for slidable, axial movement relative to said second bore;
    a plunger rod means releasably connected to said resilient plunger for moving said resilient plunger axially relative to said second bore;
    a cylindrical back stop means disposed in said inner bore above said cylindrical insert for limiting axial movement of said plunger rod means; and
    a needle attached to a bottom end of said cylindrical barrel;
    said chamfered bottom end of said cylindrical insert being spaced from said bottom end of said barrel a distance greater than the height of said resilient plunger;
    said resilient plunger being expandable to fill said inner bore when moving from said second bore into said inner bore whereby
    said resilient plunger becomes trapped between said chamfered bottom end and said bottom end of said barrel through interference between said chamfered bottom end and said resilient plunger, thereby limiting the operation of said syringe to a single injection before being disabled.

2. A single use syringe as in claim 1, wherein:

said resilient plunger includes a ball socket in a top surface thereof; and said plunger rod means includes a ball integral with a plunger rod;

said ball socket receiving said ball to connect said plunger rod means with said resilient plunger; whereby said plunger rod means and said resilient plunger become disengaged when said plunger rod means is retracted sufficiently for said top surface of said resilient plunger to engage said chamfered bottom end of said cylindrical insert.

3. A single use syringe as in claim 2, wherein:

said plunger rod further comprises a transverse cylindrical plate disposed adjacent said top surface of said plunger when said plunger is connected to said plunger rod;

said cylindrical back stop means including a bore having a diameter slightly larger than said plunger rod; whereby said transverse cylindrical plate limits the amount of retraction of the plunger rod by engagement of a top surface of said transverse cylindrical plate with a bottom surface of said cylindrical back stop means.

4. A single use syringe as in claim 1, further comprising:

a cap for covering said needle, including a funnel shaped open end for guiding said needle into said cap, an elongated tube having a bore therein connected to said funnel shaped open end, and a transverse cylindrical plate integral with said elongated tube at an end of said elongated tube opposite said funnel shaped open end; whereby said needle is covered subsequent to a first use thereof, thereby to protect a handler during disposal of said syringe, said transverse cylindrical plate being engaged by a tip of said needle to hold said cap in place.

* * * * *